United States Patent
Kim (10) Patent No.: US 10,698,044 B2
(45) Date of Patent: Jun. 30, 2020

(54) RF COIL UNIT INCLUDING DIELECTRIC STRUCTURE, AND MAGNETIC RESONANCE IMAGING SYSTEM INCLUDING THE SAME

(71) Applicant: Samsung Electronics Co., Ltd., Suwon-si (KR)

(72) Inventor: Kyoungnam Kim, Incheon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 511 days.

(21) Appl. No.: 15/507,932

(22) PCT Filed: Jan. 21, 2015

(86) PCT No.: PCT/KR2015/000614
§ 371 (c)(1),
(2) Date: Mar. 1, 2017

(87) PCT Pub. No.: WO2016/035948
PCT Pub. Date: Mar. 10, 2016

(65) Prior Publication Data
US 2017/0285118 A1   Oct. 5, 2017

(30) Foreign Application Priority Data

Sep. 1, 2014 (KR) .................. 10-2014-0115684

(51) Int. Cl.
*G01R 33/34* (2006.01)
*G01R 33/565* (2006.01)
*A61B 5/055* (2006.01)

(52) U.S. Cl.
CPC ........ *G01R 33/34046* (2013.01); *A61B 5/055* (2013.01); *G01R 33/34076* (2013.01); *G01R 33/5659* (2013.01)

(58) Field of Classification Search
None
See application file for complete search history.

(56) References Cited

U.S. PATENT DOCUMENTS 4,746,866 A * 5/1988 Roschmann ..... G01R 33/34046
324/318
6,316,941 B1 * 11/2001 Fujita ............... G01R 33/34046
324/318

(Continued)

FOREIGN PATENT DOCUMENTS

| EP | 2618170 A1 | 7/2013 |
| JP | 2005-510319 A | 4/2005 |
| KR | 10-2012-0015580 A | 8/2013 |

OTHER PUBLICATIONS

International Search Report dated May 21, 2015 in International Application No. PCT/KR2015/000614 (2 pages in English).

*Primary Examiner* — Nasima Monsur
(74) *Attorney, Agent, or Firm* — NSIP Law (57) ABSTRACT

Provided are an RF coil unit and a magnetic resonance imaging system. The RF coil unit may include a base on which RF coil elements are formed and a dielectric structure on an inner side of the base. The dielectric structure may include a plurality of dielectric structure units. The dielectric structure units may be connected to each other by connection units. The dielectric structure may include an inner space for placing an object therein. The dielectric structure includes a high dielectric material.

14 Claims, 5 Drawing Sheets

(56) References Cited

U.S. PATENT DOCUMENTS

| | | |
|---|---|---|
| 6,798,202 B2 | 9/2004 | Savelainen |
| 8,026,721 B2 | 9/2011 | Sodickson et al. |
| 8,089,281 B2 | 1/2012 | Zhai et al. |
| 8,421,462 B2 | 4/2013 | Zhai et al. |
| 2003/0071621 A1 | 4/2003 | Watkins et al. |
| 2006/0038564 A1* | 2/2006 | Findeklee ........ G01R 33/34046 324/318 |
| 2008/0129294 A1* | 6/2008 | Leussler .......... G01R 33/34046 324/318 |
| 2011/0124507 A1 | 5/2011 | Wosik et al. |
| 2011/0152670 A1 | 6/2011 | Yang |
| 2012/0280685 A1* | 11/2012 | Hadley .............. G01R 33/3415 324/309 |

* cited by examiner

FIG. 6

RF COIL UNIT INCLUDING DIELECTRIC STRUCTURE, AND MAGNETIC RESONANCE IMAGING SYSTEM INCLUDING THE SAME

CROSS-REFERENCE TO RELATED APPLICATIONS

This application is a U.S. national stage application of International Application No. PCT/KR2015/000614 filed on Jan. 21, 2015, which claims the benefit of Korean Patent Application No. 10-2014-0115684 filed on Sep. 1, 2014, in the Korean Intellectual Property Office, the entire disclosures of which are incorporated herein by reference for all purposes.

BACKGROUND

1. Field

The present disclosure relates to radio-frequency (RF) coil units and magnetic resonance imaging systems including the RF coil units.

2. Description of Related Art

In order to prevent or cure a disease, various diagnosing apparatuses for diagnosing an abnormality of a human body are used. Of the apparatuses, the magnetic resonance imaging (MRI) apparatus that uses a magnetic field generated by a magnetic force is widely used.

An MRI apparatus may take a photograph of a cross-section of a human body by using a nuclear magnetic resonance phenomenon. Atomic nuclei of hydrogen $^1$H, phosphate $^{31}$P, sodium $^{23}$Na, carbon isotope $^{13}$C, etc. may respectively have unique rotating magnetic field constants by a nuclear magnetic resonance phenomenon. After applying an electromagnetic wave to a magnetization vector of these atomic nuclei, an internal image of a human body may be obtained by receiving a magnetic resonance signal generated due to a resonance by the magnetization vector that is lain on a vertical plane. At this point, an RF coil is used for applying an electromagnetic wave to the human body to resonate the magnetization vectors in the human body and to receive the magnetic resonance signal generated due to the resonance by the magnetization vector on a vertical plane. The RF coil may be referred to as an RF antenna in a sense that the RF coil transmits an electromagnetic wave to a human body to resonate the magnetization vector and receives a magnetic resonance signal. A single RF coil may perform both functions of resonating the magnetization vector (a transmission mode) and receiving a magnetic resonance signal (a receiving mode), or the transmission mode and the receiving mode may be separately performed by including a transmission mode RF coil and a receiving mode RF coil. Also, an RF coil that performs both the transmission mode and the receiving mode may be referred to as a transceiving coil. A coil for transmission purpose may be referred to as a transmission coil, and a coil for receiving purpose may be referred to as a receiving coil.

An RF coil includes a body type RF coil that is mounted on an external part of a magnetic resonance imaging apparatus and a surface type RF coil or a volume type RF coil that is used by being attached to an object or is arranged close to the object. Since the body RF coil is installed inside the external part of the magnetic resonance imaging apparatus, the body RF coil is formed on a cylindrical type frame having a size into which an object can be placed, and thus, may be a transceiving coil or a transmission coil. The surface type RF coil or the volume type RF coil is attached to the object or is attachably and detachably installed on a table on which the object is placed, and is generally formed along the shape of a part of the object, for example, a head coil, a neck coil, a waist coil, etc. The surface type RF coil or the volume type RF coil may be a transceiving coil or a receiving coil.

SUMMARY

Provided is a magnetic resonance imaging system including an RF coil unit configured to ensure homogeneity of a magnetic field formed by a volume type RF coil.

The technical problem to be solved by the current example embodiment is not limited to the above technical problems, and may further include other technical problems.

According to an aspect of an embodiment, an RF coil unit for a magnetic resonance imaging system, the RF coil unit includes at least one RF coil element on a base having a cylindrical shape with a circular or oval shaped cross-section and a dielectric structure that is formed on an inner side of the base.

The dielectric structure may include a plurality of dielectric structure units.

The dielectric structure units may be connected to each other by connection units formed of a conductive material.

The dielectric structure units respectively may include grooves into which the connection units are inserted.

The dielectric structure may include an inner space for placing an object.

The dielectric structure may include a through hole connected to the inner space of the dielectric structure.

The dielectric structure may include a high dielectric material.

The dielectric structure may include $BaTiO_3$ or $CaTiO_3$.

The RF coil unit may be a volume type RF coil unit.

According to an aspect of an embodiment, a magnetic resonance imaging system includes: an RF coil unit including a dielectric structure that includes at least one RF coil element on a base having a cylindrical shape with a circular or oval shaped cross-section and is formed on an inner side of the base.

According to the embodiments described above, a dielectric structure is formed in an RF coil unit, and thus, a magnetic field that is generated by a volume type RF coil unit of a magnetic resonance imaging system may be applied generally to a whole object. Since a homogenous magnetic field is applied to the object, a high resolution magnetic resonance image may be obtained without degrading the quality of the magnetic resonance image according to locations.

DETAILED DESCRIPTION

Hereinafter, an RF coil unit according to an example embodiment and a magnetic resonance imaging system including the radio frequency coil (RF) coil unit will be described in detail with reference to the accompanying drawings. In the drawings, widths and thicknesses of layers or regions may be exaggerated for clarity of the specification, and like reference numerals refer to like elements.

Figure 1:
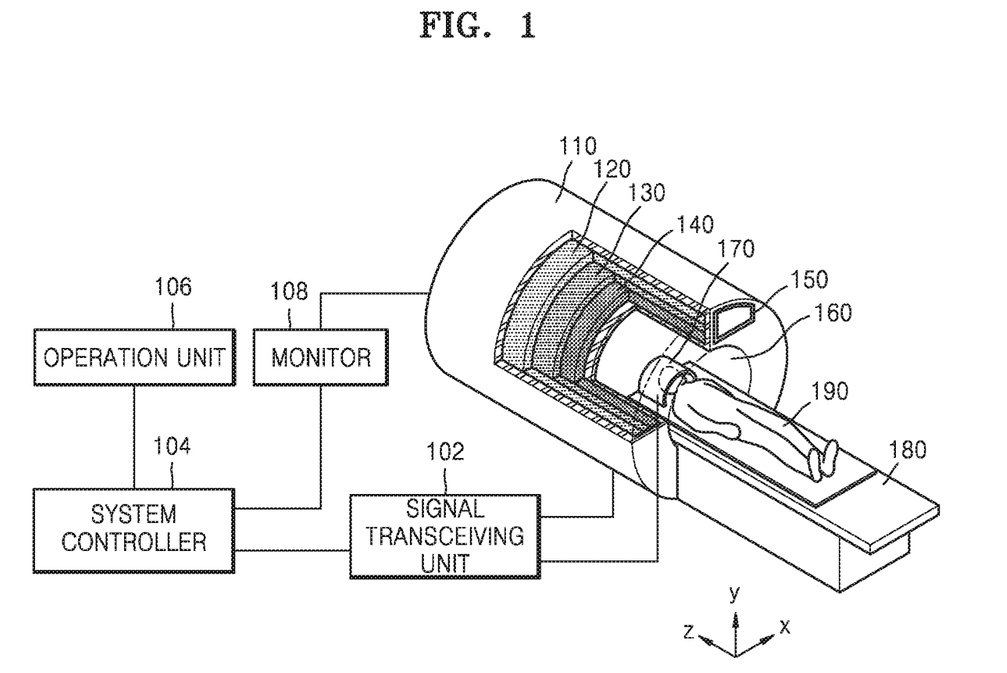
FIG. 1 is a schematic perspective view showing a configuration of a magnetic resonance imaging system according to an example embodiment.

FIG. 1 is a schematic perspective view showing a configuration of a magnetic resonance imaging system according to an example embodiment.

Referring to FIG. 1, the magnetic resonance imaging system according to the current example embodiment may include a housing 110, a main magnet 120, a gradient coil 130, and an RF coil unit 140.

The main magnet 120 may generate a static magnetic field for aligning magnetic dipole moments of nuclei of atoms in a certain direction. The atoms may be, for example, hydrogen, phosphate, sodium, and carbon that are distributed in an object 190 and generate a magnetic resonance phenomenon. The main magnet 120 may be a superconducting electromagnet that may generate a high magnetic field having an intensity of greater than, for example, 0.5 T. When the intensity and homogeneity of a magnetic field generated by the main magnet 120 is high, a relatively precise and correct magnetic resonance image with respect to the object 190 may be obtained.

In the current example embodiment, the object 190 may be a human, an animal, or a part of a human or animal. For example, the object 190 may include an organ, for example, a liver, a heart, a uterus, a breast, or a vein. Also, the object 190 may include a small animal, such as an experimental rat.

The gradient coil 130 may be formed on an inner side of the main magnet 120, and may include three gradient coils configured to generate gradient magnetic fields in an x-axis direction, a y-axis direction, and a z-axis direction that are perpendicular to each other. The gradient coil 130 may generate spatially linear gradient magnetic field to take a photograph of a magnetic resonance image. The gradient coil 130 may provide location information of each part of the object by inducing resonance frequencies different from each other in each of the parts of the object 190.

The RF coil unit 140 may be located on an inner side of the gradient coil 130. The RF coil unit 140 may constitute a cylindrical magnetic structure together with the main magnet 120 and the gradient coil 130. Also, an RF coil unit 170 may be located adjacent to the object 190 on a table 180 where the object 190 is placed. The RF coil unit 140 located on the inner side of the gradient coil 130 may be referred to as a body type RF coil unit, and the RF coil unit 170 located adjacent to the object 190 on the table 180 may be referred to as a volume type RF coil unit or a surface type RF coil unit. The RF coil unit 170 in FIG. 1 is a surface type RF coil unit, but alternatively it may be a volume type RF coil unit, so it will be referred to interchangeably as the surface type RF coil unit 170 and the volume type RF coil unit 170 for convenience of description.

The RF coil units 140 and 170, that is, the body type RF coil unit 140, the volume type RF coil unit 170, and the surface type RF coil unit 170 may generate a high frequency magnetic field with the Larmor frequency as the center frequency, and may excite an RF signal in the object 190, and may receive a magnetic resonance signal emitted from the object 190. In detail, in order to transition an atomic nucleus from a low energy state to a high energy state, the RF coil unit 140, the volume type RF coil unit 170, and the surface type RF coil unit 170 may generate an electromagnetic wave signal, for example, an RF signal having a radio frequency corresponding to the kind of atomic nucleus of the object 190 and may apply the electromagnetic wave signal to the object 190. When the electromagnetic wave signal generated by the body type RF coil unit 140, the volume type RF coil unit 170, and the surface type RF coil unit 170 is applied to an atomic nucleus, the energy level of the atomic nucleus may be transitioned from a low level energy state to a high level energy state. When the electromagnetic wave signal generated by the body type RF coil unit 140, the volume type RF coil unit 170, and the surface type RF coil unit 170 disappears, the atomic nucleus may emit an electromagnetic wave having a Larmor frequency while the energy level of the atomic nucleus to which the electromagnetic wave signal is applied is transitioning from the high level energy state to a low level energy state. That is, when the application of an electromagnetic wave signal with respect to the atomic nucleus is stopped, the energy level of the atomic nucleus to which the electromagnetic wave signal is applied is changed from a high energy level to a low energy level and an electromagnetic wave having a Larmor frequency may be emitted. The body type RF coil unit 140, the volume type RF coil unit 170, and the surface type RF coil unit 170 may receive an electromagnetic wave signal emitted from atomic nuclei inside the object 190. When the electromagnetic wave signal is demodulated to a sine wave after amplifying the received electromagnetic wave signal by using a high frequency amplifier, a magnetic resonance signal of a base band may be obtained. When the magnetic resonance signal of the base band is processed to an image, a magnetic resonance image is generated.

The body type RF coil unit 140 may be fixed on an inner side of the gradient coil 130 of the housing 110, and the volume type RF coil unit 170 and the surface type RF coil unit 170 may be attachable to and detachable from the table 180 on which the object 190 is placed. The volume type RF coil unit 170 and the surface type RF coil unit 170 may be used for diagnosing a specific part, for example, a head, a face, a leg, or an ankle of the object 190, or for diagnosing a relatively small sized object 190, for example, an experimental rat.

The housing 110 that includes the main magnet 120, the gradient coil 130, and the RF coil unit 140 may have a cylindrical shape. A bore 160 may be formed in the housing 110. The bore 160 may be a space for receiving the table 180 on which the object 190 is placed. The bore 160 may extend in the z-direction towards an inner side of the RF coil unit 140. A diameter of the bore 160 may be determined according to the sizes of the main magnet 120, the gradient coil 130, and the RF coil unit 140.

A display 150 may be mounted on an outer side of the housing 110 of the magnetic resonance imaging system, and an additional display may be mounted on an inner side of the housing 110. Predetermined information may be transmitted to a user or the object 190 through the displays mounted on inner and outer sides of the housing 110. Also, the magnetic resonance imaging system may include a signal transceiving unit 102, a system controller 104, an operation unit 106, and a monitor 108. The signal transceiving unit 102 may control an inclined magnetic field formed in the inner side of the housing 110, that is, in the bore 160, and may control the transmission and receiving of an RF signal and a magnetic resonance signal with respect to the body type RF coil unit 140, the volume type RF coil unit 170, and the surface type RF coil unit 170. The system controller 104 may control a sequence of signals formed in the housing 110. The monitor 108 may monitor or control the housing 110 and various devices mounted on the housing 110. The operation unit 106 may control an overall operation of the magnetic resonance imaging system.

Figure 2:
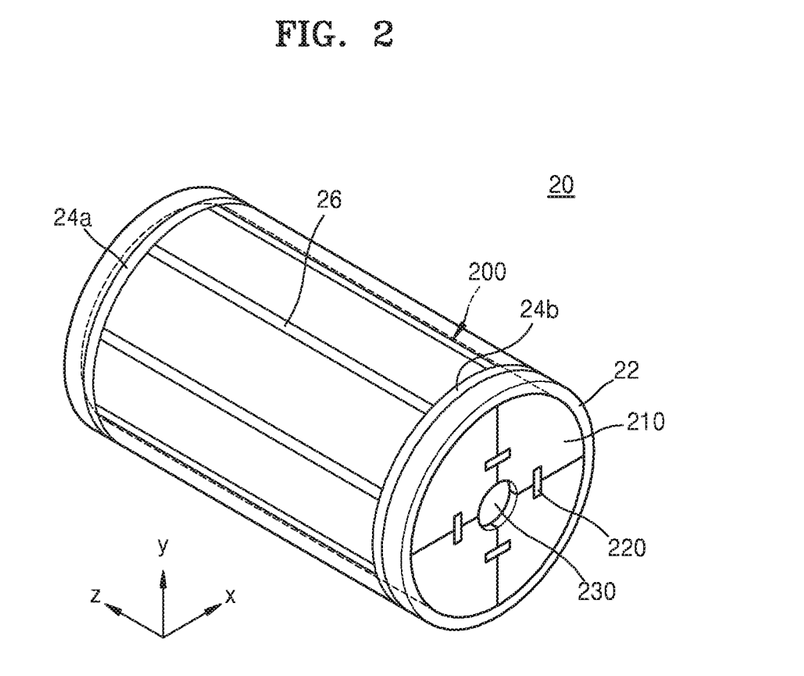
FIG. 2 is a perspective view of an RF coil unit of a magnetic resonance imaging system according to an example embodiment.
Figure 3:
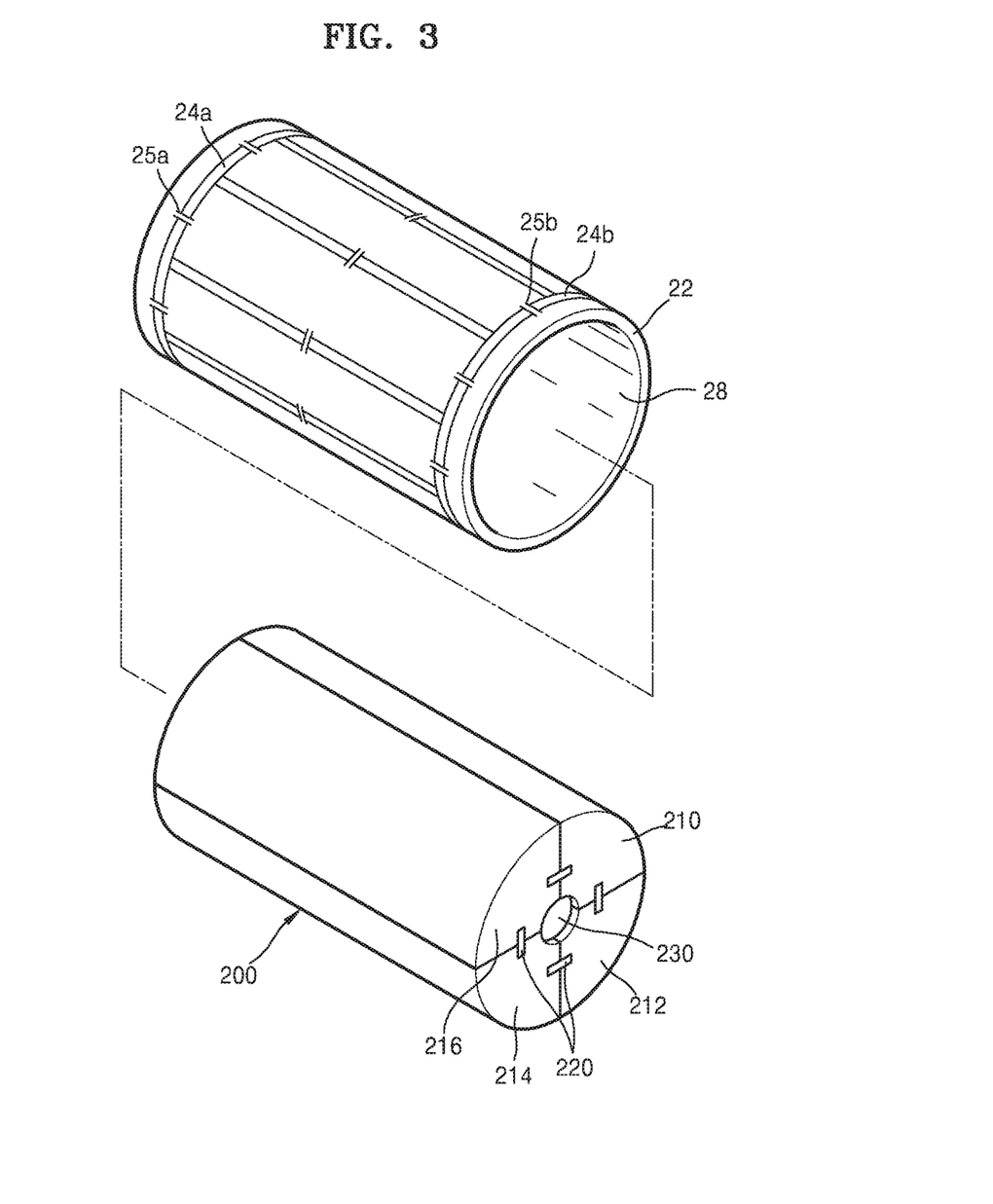
FIG. 3 is a perspective view showing a dielectric structure separated from the RF coil unit of the magnetic resonance imaging system of FIG. 2 according to an example embodiment.

FIG. 2 is a perspective view of an RF coil unit 20 of the magnetic resonance imaging system according to an example embodiment. FIG. 3 is a perspective view showing a dielectric structure separated from the RF coil unit 20 of the magnetic resonance imaging system of FIG. 2 according to an example embodiment. The RF coil unit 20 according to the current example embodiment may be the volume type RF coil unit 170 located adjacent to the object 190 of FIG. 1. However, the RF coil unit 20 may also be applied to the body type RF coil unit 140.

Referring to FIGS. 2 and 3, the RF coil unit 20 may include a base 22 on which RF coil elements 24a, 24b, and 26 are formed and a dielectric structure 200 formed by being inserted into the base 22. The RF coil elements 24a, 24b, and 26 may include a first coil element 24a and a second coil element 24b that are formed in a ring shape and surround a circumference of the base 22 and a plurality of connection units 26 that connect the first and second coil elements 24a and 24b on the base 22. The first coil element 24a and the second coil element 24b respectively may be formed near both ends of the base 22 in a z-axis direction. The connection units 26 may be expressed as legs or rods, and may be formed as a bar shape in the z-axis direction. The number of the connection units 26 may be, for example, 8 units to 32 units, but is not limited thereto. The RF coil elements 24a, 24b, and 26 formed on a surface of the base may have a birdcage shape. The RF coil elements 24a, 24b, and 26 may include capacitors 25a and 25b. A cavity 28 which is an empty space may be formed in the base 22 of the RF coil unit 20. The cavity 28 may be formed in the z-axis direction.

The dielectric structure 200 may be inserted into the cavity 28 of the base 22. The dielectric structure 200 may include a high permittivity material (or a high dielectric constant material) having a high dielectric constant higher than that of silicon oxide. The dielectric structure 200 may include a plurality of dielectric structure units 210, 212, 214, and 216, and the dielectric structure units 210, 212, 214, and 216 may be connected by connection units 220. In FIGS. 2 and 3, as an example, the dielectric structure 200 includes four dielectric structure units 210, 212, 214, and 216. However, the dielectric structure 200 may include various shapes of dielectric structure units. A through hole 230 that penetrates from an inner space of the dielectric structure 200 to the outside may be formed on at least a region of the dielectric structure 200. The through hole 230 may be formed in a z-axis direction, and as depicted in FIG. 1, in order to take a photograph of a magnetic resonance image by inserting a part of the object 190 into an inner side of the dielectric structure 200, the part of the object 190 may be inserted into the through hole 230. Also, if the object 190 is a small animal, a part of an animal, for example, a tail of the animal, may be projected to the outside through the through hole 230. The size and location of the through hole 230 are not specifically limited.

In this manner, the RF coil unit 20 according to the current embodiment may include the dielectric structure 200 inserted in the cavity 28 of the base 22, and thus, a magnetic resonance image may be photographed by locating at least a part of the object 190 in the dielectric structure 200. Since the dielectric structure 200 is included in the RF coil unit 20, a homogenous magnetic field may be applied to the whole RF coil unit 20, and as a result, a high resolution magnetic resonance image may be obtained. In detail, when a high dielectric material, that is, a medium having a high dielectric constant, is located in the RF coil elements 24a, 24b, and 26 of the RF coil unit 20, magnetic fields formed in the RF coil elements 24a, 24b, and 26 may be formed by a conductive current Jc and a displacement current Jd. At this point, the displacement current Jd is related to a dielectric constant of the dielectric structure 200 formed in the RF coil unit 20. When a high dielectric material is present in the RF coil unit 20, a second field may be formed in the RF coil unit 20, and efficiency of transmitting an RF wave to the object 190 may be increased.

The base 22 of the RF coil unit 20 according to the current example embodiment may include a relatively light material having rigidity and may include a non-magnetic material having a corrosion-resistant property and a high moldability. The base 22 may include an insulating polymer or a plastic material, for example, fiber-reinforced plastics (FRPs). Of the FRPs, the base 22 may include a glass fiber reinforced plastic-based (GFRP) complex material. The base 22 may have a cylindrical shape with ends thereof having a circular shape or an oval shape. The RF coil elements 24a, 24b, and 26 and the connection units 220 may include a patterned conductive material, for example, a patterned metal having high electrical conductivity, such as copper, silver, or gold coated copper, but the current example embodiment is not limited thereto. The dielectric structure 200 may include a material having a high dielectric constant, for example, $BaTiO_3$ or $CaTiO_3$.

For reference, when the dielectric structure 200 is mounted in the RF coil unit 20, a size of the base 22 of the RF coil unit 20 may be determined taking into consideration of the size of the dielectric structure 200, and thus, a space for placing the object 190 in the dielectric structure 200 may be ensured.

Figure 4A:
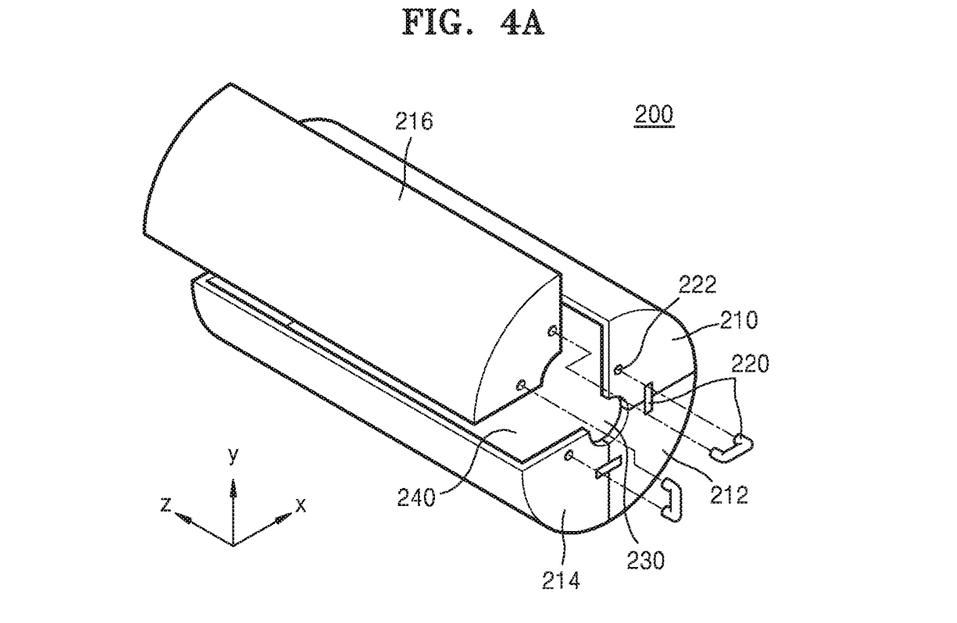
FIGS. 4A and 4B are perspective views showing dielectric structures of an RF coil unit of a magnetic resonance imaging system according to example embodiments.
Figure 4B:
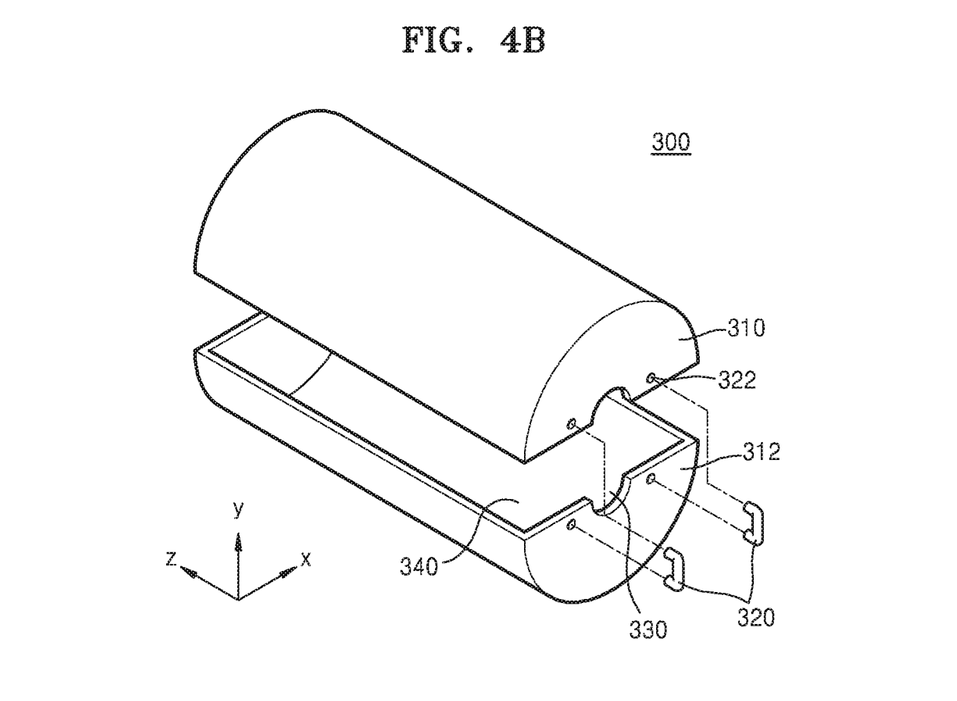

FIGS. 4A and 4B are perspective views showing dielectric structures of an RF coil unit of a magnetic resonance imaging system according to example embodiments.

Referring to FIG. 4A, the dielectric structure 200 includes the first through fourth dielectric structure units 210, 212, 214, and 216, and the first through fourth dielectric structure units 210, 212, 214, and 216 are connected to each other by the connection units 220. The first through fourth dielectric structure units 210, 212, 214, and 216 respectively include grooves 222 into which the connection units 220 are inserted. When the first through fourth dielectric structure units 210, 212, 214, and 216 are coupled, an inner space 240 for placing the object 190 may be formed.

Referring to FIG. 4B, a dielectric structure 300 includes two dielectric structure units 310 and 312. The dielectric structure units 310 and 312 may be connected to each other by connection units 320, and respectively includes grooves 322 into which the connection units 320 are inserted. When the dielectric structure units 310 and 312 are coupled to each other, an inner space 340 for placing the object 190 may be formed in the dielectric structure 300.

In FIGS. 4A and 4B, the dielectric structure 200 includes the first through fourth dielectric structure units 210, 212, 214, and 216 (refer to FIG. 4A) and the dielectric structure 300 includes the dielectric structure units 310 and 312 (refer to FIG. 4B), but the current example embodiment is not limited thereto. That is, the number of dielectric structure units to be included in the dielectric structures 200 and 300 is not specifically limited, and the locations and diameters of the through holes 230 and 330 may be selectively determined.

Figure 5:
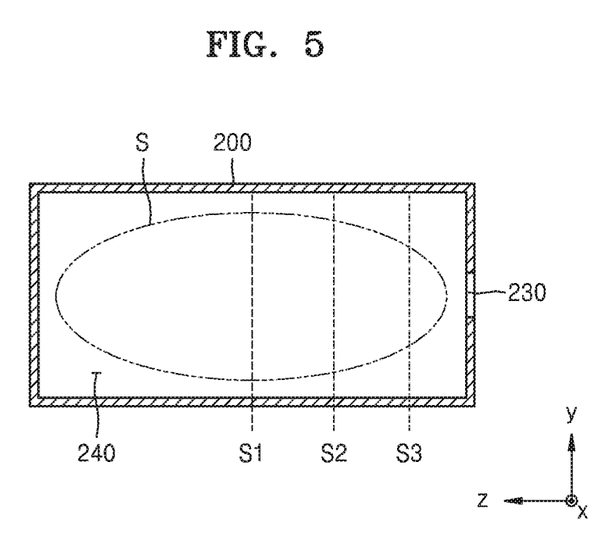
FIG. 5 shows a region of an object in a dielectric structure of an RF coil unit of a magnetic resonance imaging system according to an example embodiment.

FIG. 5 shows a region of an object in the dielectric structure 200 of the RF coil unit 20 of a magnetic resonance imaging system according to an example embodiment.

The object to be photographed by magnetic resonance imaging may be placed in the inner space 240 of the dielectric structure 200. All of the object or a part of the object may be placed in the inner space 240 of the dielectric structure 200. If a part of the object is placed in the dielectric structure 200, a remaining part of the object may be placed outside the dielectric structure 200 through the through hole 230. At this point, parts of an interest region S may be indicated as S1, S2, and S3 according to the part to be photographed by magnetic resonance imaging. A magnetic field formed in the RF coil unit of the magnetic resonance imaging system according to the current example embodiment may generally have a homogenous magnetic intensity value, as will be described with reference to FIG. 6.

Figure 6:
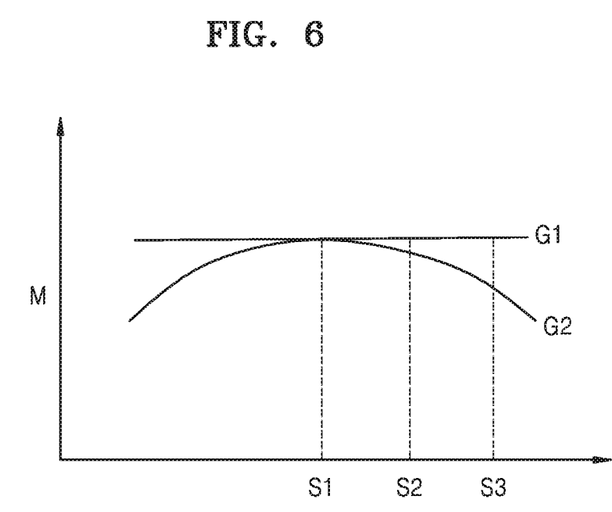
FIG. 6 is a graph showing the intensity of a magnetic field in a region of an RF coil unit of a magnetic resonance imaging system according to an example embodiment.

FIG. 6 is a graph showing the intensity of a magnetic field in a region of an RF coil unit of a magnetic resonance imaging system according to an example embodiment. Here, a horizontal axis indicates parts S1, S2, and S3 of the interest region S to be photographed by magnetic resonance imaging, and a vertical axis indicates an intensity of a magnetic field. A graph G1 indicates a magnetic intensity in the RF coil unit including the dielectric structure 200, and a graph G2 indicates a magnetic value in the RF coil unit that does not include the dielectric structure 200.

Referring to FIG. 6, it may be confirmed that the intensity (graph G1) of the magnetic field in the RF coil unit including the dielectric structure 200 is generally homogenous over the parts S1, S2, and S3. However, in the case when the dielectric structure 200 is not included in the RF coil unit, it may be confirmed that the intensity (graph G2) of the magnetic field in the RF coil unit gradually decreases from a center region towards an end region in the z-axis direction. For reference, the intensities of the magnetic fields at the S1 part in graphs G1 and G2 may be the same as they are in FIG. 6, or may be different.

As described above, in the magnetic resonance imaging system according to the current example embodiment, the RF coil unit may be modified in various forms according to locations of an interest region of an object to be diagnosed, and the homogeneity of a magnetic field formed in the RF coil unit may be increased regardless of the location of the interest region of the object.

While this inventive concept has been particularly shown and described with reference to embodiments thereof, it will be understood by those of ordinary skill in the art that various changes in form and details may be made therein without departing from the spirit and scope of the inventive concept as defined by the appended claims. For example, the RF coil unit described above may be applied to a volume type RF coil unit of a magnetic resonance imaging system, and may also be applied to a body type RF coil unit.

Therefore, it should be understood that embodiments described above should be considered in a descriptive sense only and not for purposes of limitation. The scope of the inventive concept is defined not by the detailed description of the inventive concept but by the appended claims, and all differences within the scope will be construed as being included in the inventive concept.

What is claimed:

1. An RF coil unit for a magnetic resonance imaging system, the RF coil unit comprising:
   a base having a cylindrical shape with a circular or oval shaped cross-section;
   at least one RF coil element disposed on the base; and
   a dielectric structure disposed inside the base,
   wherein the base and the dielectric structure are separate structures,
   the dielectric structure comprises a hollow cylindrical dielectric structure with a circular or oval shaped cross-section, and
   the hollow cylindrical dielectric structure comprises:
   an outer cylindrical surface conforming to an inner side of the base;
   end surfaces at opposite ends of the hollow cylindrical dielectric structure at least partially covering open ends of the hollow cylindrical dielectric structure; and
   an inner space configured to receive an object.

2. The RF coil unit of claim 1, wherein the hollow cylindrical dielectric structure comprises a plurality of dielectric structure units.

3. The RF coil unit of claim 2, wherein the dielectric structure units are connected to each other by connection units made of a conductive material.

4. The RF coil unit of claim 3, wherein the dielectric structure units respectively comprise grooves into which the connection units are inserted.

5. The RF coil unit of claim 1, wherein the hollow cylindrical dielectric structure comprises $BaTiO_3$ or $CaTiO_3$.

6. The RF coil unit of claim 1, wherein the RF coil unit is a volume type RF coil unit.

7. The RF coil unit of claim 1, wherein one of the end surfaces comprises a through hole connected to the inner space of the hollow cylindrical dielectric structure and configured to receive the object.

8. A magnetic resonance imaging system comprising:
   an RF coil unit comprising:
   a base having a cylindrical shape with a circular or oval shaped cross-section;
   at least one RF coil element disposed on the base; and
   a dielectric structure disposed inside the base,
   wherein the base and the dielectric structure are separate structures,
   the dielectric structure comprises a hollow cylindrical dielectric structure with a circular or oval shaped cross-section, and
   the hollow cylindrical dielectric structure comprises:
   an outer cylindrical surface conforming to an inner side of the base;
   end surfaces at opposite ends of the hollow cylindrical dielectric structure at least partially covering open ends of the hollow cylindrical dielectric structure; and
   an inner space configured to receive an object.

9. The magnetic resonance imaging system of claim 8, wherein the hollow cylindrical dielectric structure comprises a plurality of dielectric structure units.

10. The magnetic resonance imaging system of claim 9, wherein the dielectric structure units are connected to each other by connection units made of a conductive material.

11. The magnetic resonance imaging system of claim 10, wherein the dielectric structure units respectively comprise grooves into which the connection units are inserted.

12. The magnetic resonance imaging system of claim 8, wherein the hollow cylindrical dielectric structure comprises $BaTiO_3$ or $CaTiO_3$.

13. The magnetic resonance imaging system of claim 8, wherein one of the end surfaces comprises a through hole connected to the inner space of the hollow cylindrical dielectric structure and configured to receive the object.

14. An RF coil unit for a magnetic resonance imaging system, the RF coil unit comprising:
   a hollow cylindrical base;
   an RF coil disposed on an outer surface of the hollow cylindrical base; and
   a hollow cylindrical dielectric structure disposed inside the hollow cylindrical base and comprising end surfaces at opposite ends of the hollow cylindrical dielectric structure at least partially covering open ends of the hollow cylindrical dielectric structure,
   wherein the hollow cylindrical base and the hollow cylindrical dielectric structure are separate structures.

* * * * *